US012778589B2

(12) United States Patent
Leinwand et al.

(10) Patent No.: US 12,778,589 B2
(45) Date of Patent: Nov. 3, 2026

(54) ENHANCED TROCAR

(71) Applicant: FAMIS Devices LLC, Schoolcraft, MI (US)

(72) Inventors: Michael Jeffrey Leinwand, Kalamazoo, MI (US); Jorden Scott Kegeler, Kalamazoo, MI (US); Peter Allen Gustafson, Schoolcraft, MI (US); Graham Lark Peterson, Chicago, IL (US)

(73) Assignee: Famis Devices, LLC, Schoolcraft, MI (US)

( * ) Notice: Subject to any disclaimer, the term of this patent is extended or adjusted under 35 U.S.C. 154(b) by 1359 days.

(21) Appl. No.: 17/644,171

(22) Filed: Dec. 14, 2021

(65) Prior Publication Data

US 2022/0183692 A1 Jun. 16, 2022

Related U.S. Application Data

(60) Provisional application No. 63/126,008, filed on Dec. 16, 2020.

(51) Int. Cl.

| | |
|---|---|
| ***A61B 17/00*** | (2006.01) |
| ***A61B 17/12*** | (2006.01) |
| ***A61B 17/32*** | (2006.01) |
| ***A61B 17/3205*** | (2006.01) |
| ***A61B 18/14*** | (2006.01) |
| *A61B 17/34* | (2006.01) |

(Continued)

(52) U.S. Cl.

CPC .................. *A61B 17/12013* (2013.01); *A61B 17/320016* (2013.01); *A61B 18/1487* (2013.01); *A61B 2017/00353* (2013.01); *A61B 2017/00823* (2013.01); *A61B 2017/320064* (2013.01); *A61B 17/32056* (2013.01)

(58) Field of Classification Search

CPC ...... A61B 17/12013; A61B 17/320016; A61B 17/32056; A61B 17/3417; A61B 17/3421; A61B 17/12009; A61B 2017/00823; A61B 2017/320064; A61B 2017/00353; A61B 2017/32004; A61B 2017/12018; A61B 18/1487; A61B 2018/1407; A61B 2090/037

See application file for complete search history.

(56) References Cited

U.S. PATENT DOCUMENTS 5,462,562 A 10/1995 Elkus
5,925,044 A * 7/1999 Hofmann ........... A61B 17/3476 606/45
7,988,670 B2 8/2011 Smith (Continued)

FOREIGN PATENT DOCUMENTS

RU 2223004 2/2004
WO WO-9934736 A1 * 7/1999 ....... A61B 17/12013

*Primary Examiner* — Shaun L David
*Assistant Examiner* — Lindsey R. Rivers
(74) *Attorney, Agent, or Firm* — Rebecca J. Brandau

(57) ABSTRACT

An enhanced trocar for laparoscopic surgery has a proximal end, a distal end, and a tubular trocar body connecting and extending between the ends. The trocar body is shaped and sized to receive inline and retain therein tissue isolated and divided during a laparoscopic surgical procedure, to permit a surgeon to remove such tissue from the surgical site and dispose of the removed tissue without an additional dedicated disposal device.

8 Claims, 13 Drawing Sheets

(51) Int. Cl.
*A61B 18/08* (2006.01)
*A61B 90/00* (2016.01)

(56) References Cited

U.S. PATENT DOCUMENTS

| | | | |
|---|---|---|---|
| 9,078,699 | B2 | 7/2015 | Smith |
| 10,849,604 | B2 | 12/2020 | Yang |
| 2007/0225734 | A1 | 9/2007 | Bell |

* cited by examiner

ENHANCED TROCAR

CROSS REFERENCE TO RELATED APPLICATION

This application relies upon and claims the benefit of the filing date of U.S. Provisional Patent Application Ser. No. 63/126,008, filed Dec. 16, 2020, entitled Trocar, the entirety of which is incorporated herein by reference.

FIELD OF THE INVENTION

The present invention relates generally to surgical trocars, and, more particularly, to a multi-functional laparoscopic trocar, enhanced such that it eliminates the need for a surgeon to repeatedly change instruments during a given procedure, thus making the surgical procedure more efficient, as it can be accomplished more efficiently with fewer steps. An operation performed with the presently described and claimed trocar can therefore be expected to be performed in significantly less time as compared with a similar procedure performed with previously used conventional instruments.

BACKGROUND OF THE INVENTION

Previous surgical trocars, for example, those typically used for operations such as appendectomies, have been limited in functionality, generally permitting introduction of a single instrument to perform one surgical task, removing that instrument and then introducing another separate instrument into the surgical site to perform a second task, and so on.

Appendectomies are one of the most common surgical operations performed, with more than 300,000 such operations completed in the United States each year. About 90% of these operations are performed laparoscopically. A laparoscopic appendectomy generally involves inserting multiple instruments into the abdominal cavity of a patient via trocars. Typically, in such an operation, the mesoappendix, which contains the blood supply to the appendix, is divided (separated from the appendix), followed by ligation of the appendix at the point of its attachment with the cecum, and then excision of the appendix. The appendix is then removed from the patient's abdominal cavity, usually via a retrieval bag. Such a procedure can be accomplished various ways using different instrumentation. One common way, as illustrated schematically in FIG. 13, is to use known endo-stapling devices which place rows of staples on each side of the planned cutting site, then cutting in between the rows of staples, thus sealing the wound on each side of the cut and dividing (separating the tissue) between two closed edges. This technique is used for separating the mesoappendix and the appendix. Another known surgical strategy, illustrated schematically in FIG. 14, is to utilize electrocautery to divide the mesoappendix, suture ligatures to ligate two areas on the appendix, then follow by cutting between the two ligatures with laparoscopic scissors. A retrieval bag ("endo-bag") is then placed into the abdomen, the appendix is placed into it, and then the bag containing the divided appendix is removed from the abdominal cavity. Both of these examples of known techniques involve several steps of passing different instruments back and forth, often through multiple trocars, which is tedious and time-consuming. Further, the switching back and forth of various instruments, via the trocar(s) increases the opportunity for injury to intraperitoneal organs.

Thus, there has been a long-felt need in the medical industry for an economically manufactured surgical trocar which permits the surgeon to perform appendectomies, for example, and other laparoscopic procedures much more efficiently.

SUMMARY OF THE INVENTION

Accordingly, the present invention is, briefly, an enhanced trocar for laparoscopic surgery. The trocar has a proximal end, a distal end and a tubular trocar body connecting and extending between the proximal end and the distal end. The enhanced trocar body is shaped and sized to receive inline and retain therein tissue isolated and divided during a laparoscopic surgical procedure, thereby permitting a surgeon to remove such tissue from a surgical site and dispose of the removed tissue without an additional dedicated disposal device. The new enhanced trocar has at least one mechanism for isolating and dividing the tissue within the body of the trocar, which mechanism for isolating and/or dividing the tissue within the body of the trocar can be at least one filament connected to the trocar, a blade within the trocar, and/or an endo-stapling device for selective application by the surgeon to the tissue.

The invention further includes, briefly, the new enhanced trocar having at least two filaments including a first surgical ligature and a second surgical ligature for isolating and/or dividing tissue within the body of the trocar and at least one of the surgical ligatures can be formed to selectively break-away, to thereby permit release from the trocar of any tied-off tissue remaining at the surgical site.

The invention further includes, briefly, the first surgical ligature and the second surgical ligature each having a ligature loop and a sliding ligature knot or other non-reversable tightening mechanism at respective distal ends of the first surgical ligature and the second surgical ligature, to thereby permit selective manipulation by the surgeon of the first surgical ligature and the second surgical ligature, to separately set the tension of the respective ligature knots and cause tightening of the respective loops thereof to selectively tie-off tissue during a surgical procedure while the tissue is within the body of the enhanced trocar.

The new enhanced trocar also includes, briefly, a surgical wire operably connected to the proximal end of the trocar and extending toward the distal end of the trocar body. The surgical wire can have a loop at the distal end thereof, the loop being removably attached around an interior wall of the trocar body to thereby permit selective release and manipulation by the surgeon of the wire loop to divide tissue within the trocar body. The ligature loops and the surgical wire can each be removably attached around an interior wall of the trocar body, so as to avoid interfering with the path of any surgical instruments passing through the distal end of the trocar until the corresponding loop is selectively released from the interior wall of the trocar by the surgeon.

The invention is also, briefly, that each of the surgical ligatures and the surgical wire, can have a corresponding aperture in the trocar body distal wall for passage therethrough of the corresponding filament. The loop at the distal end of each surgical filament can be connected to the corresponding loop inside of the corresponding aperture by a slidable knot or other irreversible tightening mechanism. In this manner proximal urging of a ligature by the surgeon via a corresponding lever, arm or other controller attached to the ligature, causes closing of the corresponding ligature loop through the knot of that ligature and around any tissue therein. A similar arm, lever, or other controller connected to the surgical wire at the proximal end of the trocar permits the surgeon to manipulate the surgical wire, applying pressure to tissue within the wire loop to sever the tissue to be retained in the trocar body away from tissue that has been securely tied off and left at the surgical site.

The present invention may also include, briefly, at least one motor attached to the trocar body for powering selective operation by the surgeon of at least a portion of the at least one mechanism for isolating and dividing the tissue within the body of the trocar. A further aspect of the present invention is that the at least one mechanism for isolating and dividing the tissue within the body of the trocar can include a concentric double wall for passage therebetween of the at least one surgical filament and control of thereof by twisting of the concentric walls relative to one another.

A wide variety of applications and installations are available for the new enhanced laparoscopic trocar. While the discussion and drawings herein focus primarily on use of the new trocar for performing laparoscopic appendectomies, it will be clear to the experienced surgeon that there are many instances in other laparoscopic procedures during which the present invention will be very useful.

Accordingly, various embodiments of the invention include: a device that can be used to perform multiple aspects of an operation, such as an appendectomy; a device that can be used to perform some or all of the functions of trocar, ligatures, cutting, and retrieval systems within a single trocar device; and provide an in-line approach which is simpler and thus is a more efficient system for removing the appendix and may be used for other tissues as well.

The various embodiments of the invention further include a surgical instrument having a multi-function trocar that advantageously reduces operative duration. As an appendectomy trocar, some embodiments of the invention permit use for ligating the appendix, dividing the appendix, and also serve as the retrieval system, obviating the need for a stapling device, endoscopic ligatures, endoscopic scissors and a specimen retrieval bag.

The enhanced trocar according to various embodiments accomplishes multiple steps of the usual laparoscopic appendectomy operation inside a single trocar device. The device serves as a trocar while also ligating, cutting, and retrieving divided tissue.

Further areas of applicability of the present invention will become apparent from the drawings and detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features and advantages of the present invention will become more fully understood from the accompanying drawings, wherein.

Throughout the drawings like element numbers indicate like parts. Some elements are omitted from some figures for clarity and simplicity of the drawings. The drawings are not necessarily made to scale. In reference to the drawings, the terms "Fig." and "Figure" may be used interchangeably.

DETAILED DESCRIPTION OF USEFUL EMBODIMENTS

Figure 7:
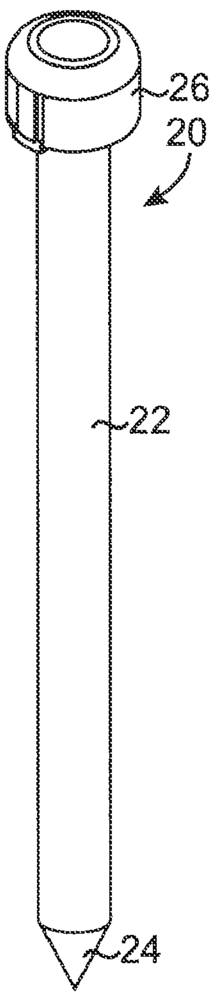
FIG. 7 is perspective view of an obturator useful with the trocar of FIG. 1, as a part of the enhanced trocar assembly.
Figure 8:
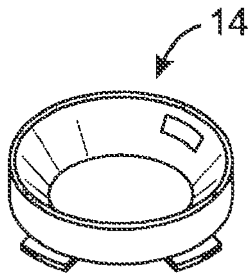
FIG. 8 is a perspective view of a ring on the proximal end of the trocar of FIG. 1.

With reference to the attached drawings, FIGS. 1 through 6 show various views of a preferred embodiment of an enhanced trocar, generally designated 10, constructed in accordance with and embodying the present invention. Trocar 10 includes a generally tube-shaped body or barrel 12 having a ring 14 on the proximal end 16 of barrel 12. Trocar body 12 terminates at an open distal end 18. Proximal end 16 of trocar 10 receives an obturator (seen best in FIG. 7), generally designated 20, which obturator includes an elongated body 22 having a pointed distal end 24, which extends in use through the open distal end 18 of the trocar. A cap 26 at the proximal end of obturator 20 seats on ring 14 at the proximal end of trocar 10 when the obturator is in operative position within trocar body 12. Ring 14 is also illustrated in FIG. 8, and has been enlarged for clarity of a useful construction thereof for secure connection to the proximal end of trocar body 12, and showing a downwardly and inwardly sloping inner side wall to facilitate insertion of other instruments, such as obturator 20, for example, into trocar body 12.

It is to be understood that throughout this document, unless otherwise specified, the terms "distal" and "proximal" are used to refer to the position of a surgical instrument in relation to the surgeon, not the patient. Thus, for example, the surgeon may hold the proximal end of a trocar and insert the distal end of an obturator into the proximal end of the trocar and through the trocar into a patient (away from the surgeon) to facilitate insertion and placement of the trocar for use in a laparoscopic surgery.

Figure 1:
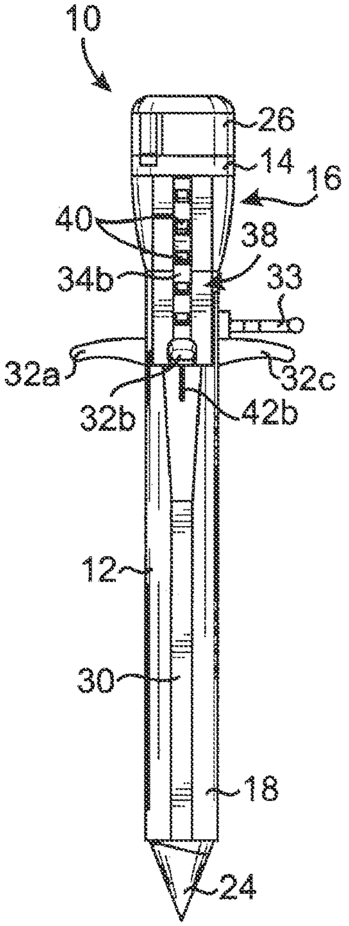
FIG. 1 is a front elevational view of an enhanced trocar device constructed in accordance with and embodying the present invention.
Figure 10:
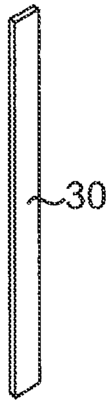
FIG. 10 is a perspective view of the track cover of the trocar of FIG. 1.

The position of trocar 10 in FIG. 1 reveals a longitudinal cover 30 which extends along at least part of the length of barrel 12. Cover 30, in the present embodiment, is shown as a single cover over a single slot 28, which is effectively a groove formed in barrel 12. FIG. 2B shows enhanced trocar 10 with longitudinal slot 28 shown uncovered; i.e., without cover 30 in place, to illustrate that slot 28 is formed longitudinally along the exterior of a portion of the distally directed end of trocar barrel 12. Slot 28 serves to house portions of the lengths of various filaments, specifically, in this embodiment, ligatures and an electrocautery wire, which are illustrated and discussed in greater detail later herein. The elongated slot cover 30 discussed above is also shown in FIG. 10, for clarity, and serves to enclose a slot 28 and to cover the filaments therein. While this is the presently preferred shape and location of slot 28 and cover 30, other configurations can be conceived which will function appropriately as alternative embodiments of the present invention. Indeed, alternative methods of construction may accommodate appropriate disposition of the various filaments on or within trocar body 12 without the necessity of a track and cover.

Figure 2:
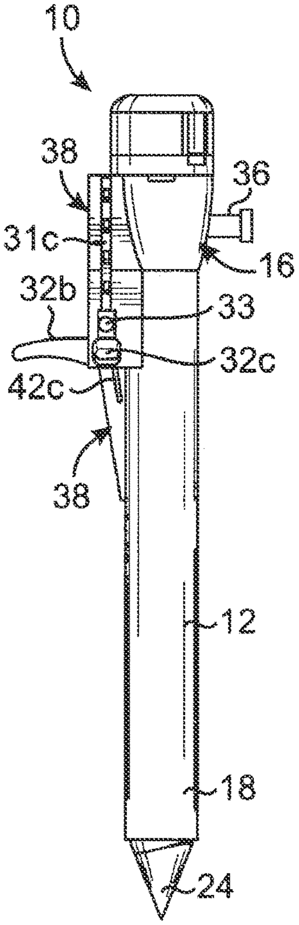
FIG. 2 is a side elevational view of the trocar of FIG. 1.
Figure 3:
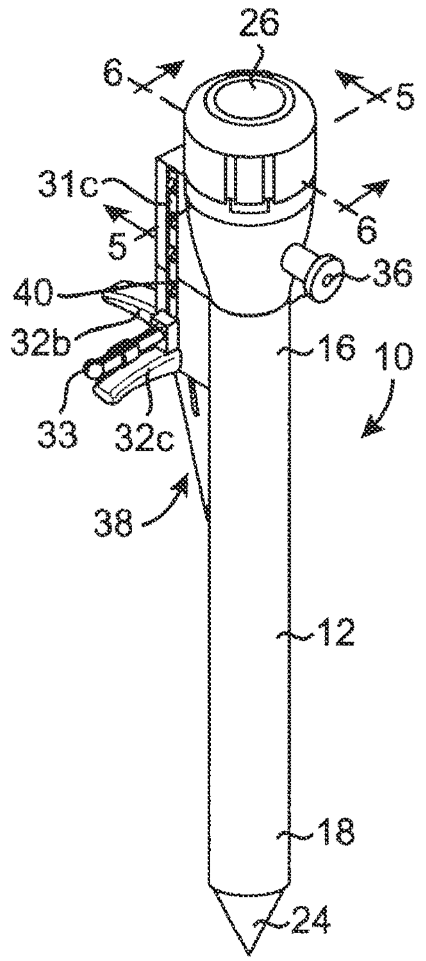
FIG. 3 is a perspective view of the trocar of FIG. 1, rotated approximately 180 degrees and tilted from the top end, slightly forward and right with respect to FIG. 1.
Figure 4:
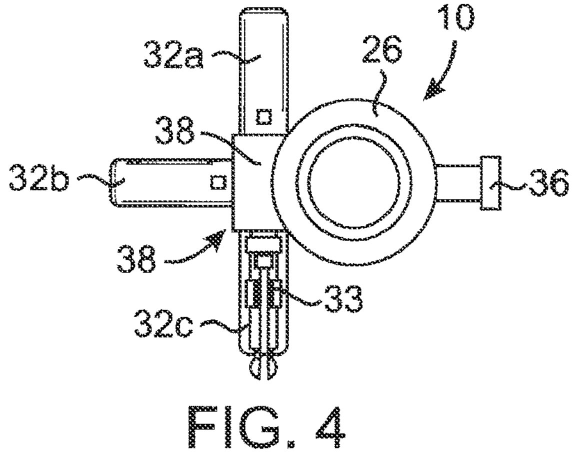
FIG. 4 is a top plan view of the trocar of FIG. 2, showing the relative positions of the arms, obturator and air inlet in a useful embodiment of the invention.
Figure 5:
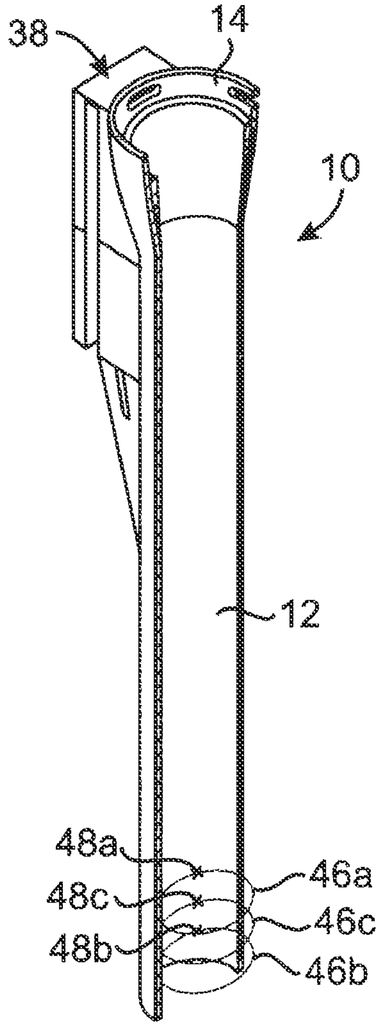
FIG. 5 is a longitudinal sectional view of the trocar of FIG. 1, taken on line 5-5 of FIG. 3, shown without the arms and some other elements.
Figure 6:
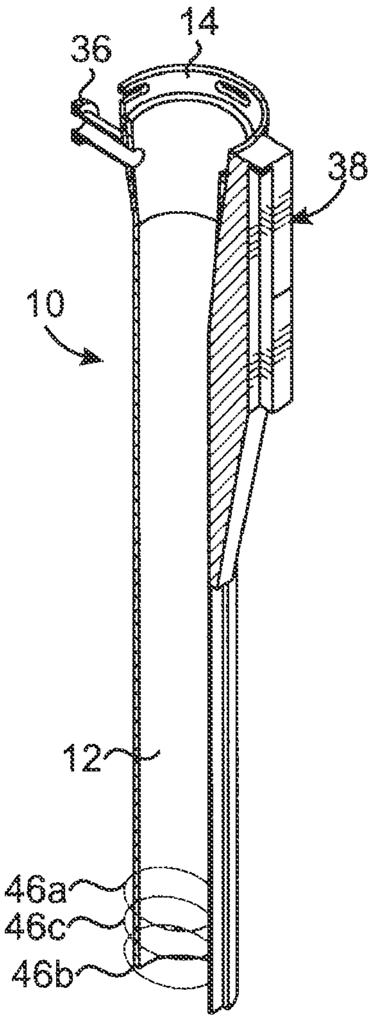
FIG. 6 is longitudinal sectional view of the trocar of FIG. 1, taken on line 6-6 of FIG. 3, shown without the arm and some other elements.
Figure 9:
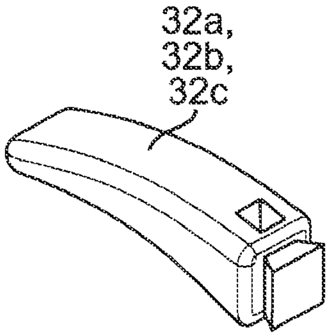
FIG. 9 is a perspective view of a ligature control arm of the trocar of FIG. 1.

FIGS. 1-4 illustrate trocar 10 from various angles and points around the circumference thereof in order to clearly illustrate the location of three arms 32*a*, 32*b*, 32*c*, each of which arms (shown enlarged in FIG. 9) are preferably operably connected to the proximal end of trocar 10 via an arm hub, generally designated 38 and best seen in FIGS. 3, 5 and 6. Arm hub 38 can reasonably have a variety of useful general forms in keeping with the present invention, but is preferably formed as shown in the drawings with three exterior walls, each wall having a longitudinal track, indicated at 31*a*, 31*b*, 31*c* for movable passage there-along of a corresponding one of arms 32*a*, 32*b*, 32*c*. Alternatively, another useful form, not shown, of the new trocar can have each arm attached more directly to the proximal end of trocar 10, rather than with an intervening hub.

In several of the figures there is visible, just above arm 32*c*, a metal connector 33 for selective attachment to an electrocautery device of known variety or any suitable newly developed substitute. Along the interior length of each arm track 31*a*, 31*b*, 31*c* are formed spaced-apart steps or nubs 40 to serve as selectable stops for the arm in each corresponding track. Each arm could also be usefully formed in other ways to still be attached to and capable of controlling the position of the associated filaments and could take other forms such as a button, zip-tie or other positionable mover.

Figure 2A:
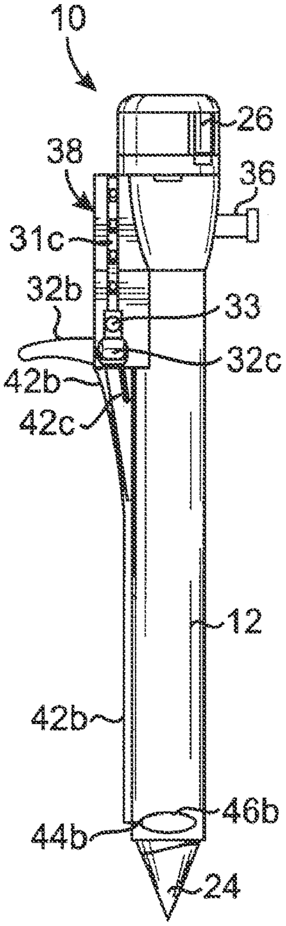
FIG. 2A is the same as FIG. 2 with the addition of a ligature illustrated on the left side of the figure, extending from an arm on the outer surface of the trocar, along the body of the trocar toward the distal end, passing through the body and terminating in a knotted loop inside the trocar.
Figure 2B:
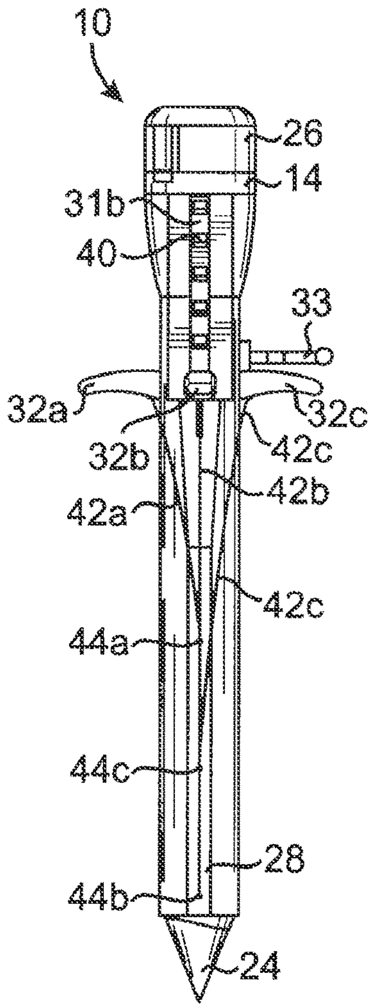
FIG. 2B is an elevational view of the trocar of FIG. 1, without the track cover and illustrating a useful configuration of the ligatures and wire.

A preferred arrangement of arms 31*a*, 31*b* and 31*c* with respect to their corresponding filaments is best illustrated in FIGS. 2A and 2B, and to some extent in FIGS. 1 and 2. As shown in FIG. 2B, filament 42*a* is connected to arm 32*a* and filament 42*b* is connected to arm 32*b*. In this embodiment both filaments 42*a* and 42*b* are ligatures. At the right side of FIG. 2B, however, filament 42*c*, which is connected to arm 32*c* is a wire of a known type used in association with electrocautery instruments. As illustrated in FIG. 2B, each of the three filaments 42*a*, 42*b*, 42*c* passes from its associated arm, lever, button, or other device or mover toward and into slot 28 where they are housed to prevent tangling and possible damage to the filaments.

Shown in FIG. 2B are three apertures 44*a*, 44*b*, 44*c* for receipt of the corresponding filaments 46*a*, 46*b*, 46*c*. In this figure the apertures are shown significantly spaced out along the length of trocar barrel 12, for clarity and ease of seeing the arrangement. Spatially separated apertures 44*a*, 44*b*, 44*c* are provided through the distal end wall of slot 28 for passage therethrough of a corresponding filament 42*a*, 42*b*, 42*c* into the interior of trocar body 12. FIG. 2A schematically illustrates an example of one of the ligatures, 42*b*, on the exterior of body 12 for purposes of illustration only, passing from its point of attachment to arm 32*b* toward the open distal end of trocar 10 where ligature 42*b* passes through aperture 44*b*, to the interior of the trocar. FIGS. 5 and 6 are sectional views in which it is easier to see a preferred location for each filament loop, closer to each other than shown in FIG. 2*b*, and substantially adjacent the interior distal end of trocar body 12. The purpose of this preferred location for filament loops 46*a*, 46*b*, 46*c* on their respective filaments 42*a*, 42*b*, and 42*c* within trocar 10 will become apparent in the more detailed discussion below.

In use, selective pulling (proximal) pressure by the surgeon on any of the three arms 32*a*, 32*b*, 32*c* will urge the selected arm away from the corresponding filament aperture. If the selected arm controls one of the ligature filaments 42*a*, 42*b* this action will cause the ligature filament to move upwardly in the filament slot and the associated filament loop will be caused to tighten around adjacent tissue within the trocar body as the corresponding slip knot 48*a*, 48*b* is pulled against the internal trocar body wall. In the case of wire filament 42*c* there is preferably no knot, but more likely a weld point, or other secure connection, so by proximal urging of arm 32*c* wire 42*c* will move upwardly (toward the surgeon) in the covered slot or trench 28, causing pulling force on the wire loop 46*c* and wire weld 48*c*. In this manner the new enhanced trocar 10 with various filaments can be used to sever tissue, as in the present preferred embodiment, with use of an attached electrocautery device whereby wire filament 42*c* attached to arm 32*c* can be used to sever tissue by pressure alone, or selectively by burning through the tissue within the heated wire loop 46*c*.

In FIG. 2B the apertures 44a, 44b, 44c are each shown as being formed through the trocar wall for passage therethrough of the appropriate filament. It should be understood, the filament apertures in FIG. 2 are shown disposed along the length of trocar 20 so as to be spaced apart at a significant distance, sufficient that the structure and arrangement of filaments can be clearly seen in the figures. Nonetheless, the three filament apertures 44a, 44b, 44c in such a useful embodiment can and likely will instead be disposed as illustrated in FIGS. 5 and 6, being much closer together than as shown in FIG. 2B, which is intended to indicate the positions of the three filaments and their corresponding knots or weld, relative to each other in a preferred embodiment of enhanced trocar 20 for use in the example of a laparoscopic appendectomy.

Figure 12A:
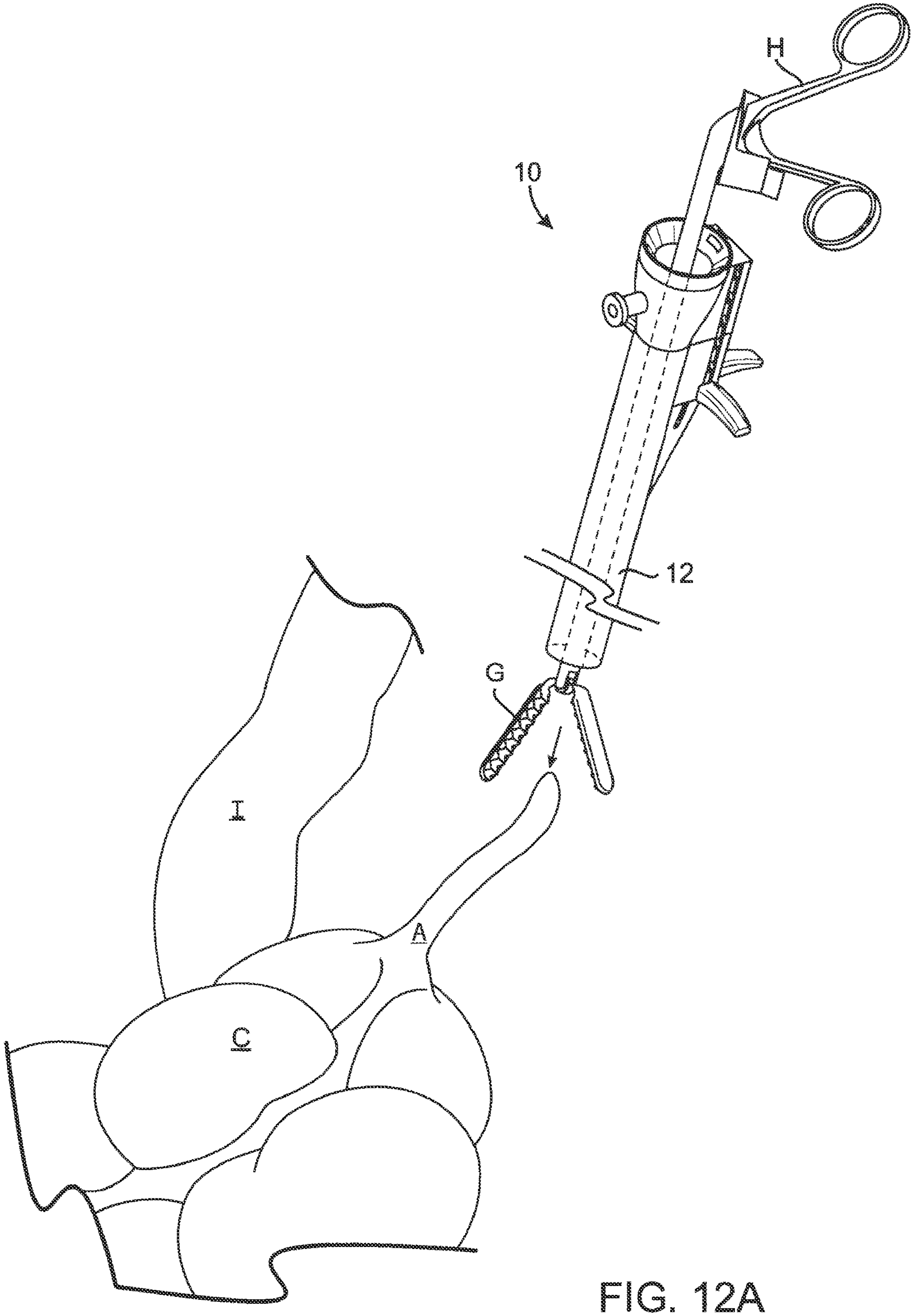
FIG. 12A is a perspective view of the grasping element of the trocar of FIG. 1 illustrating an approach of the device toward a schematically shown appendix.

FIGS. 12A through 12E schematically illustrate five main steps of an otherwise substantially routine laparoscopic appendectomy operation, but using an illustrative embodiment of the present enhanced trocar. The schematic figures include elements of a human digestive tract including the ileum I as it empties into the cecum C and the attached appendix A. FIG. 12A includes a partial schematic perspective view of the body/barrel 12 of the new enhanced trocar 10 with the open gripping end G of a known grasping instrument within trocar barrel 12 for gripping the appendix prior to surgical removal thereof.

Figure 12B:
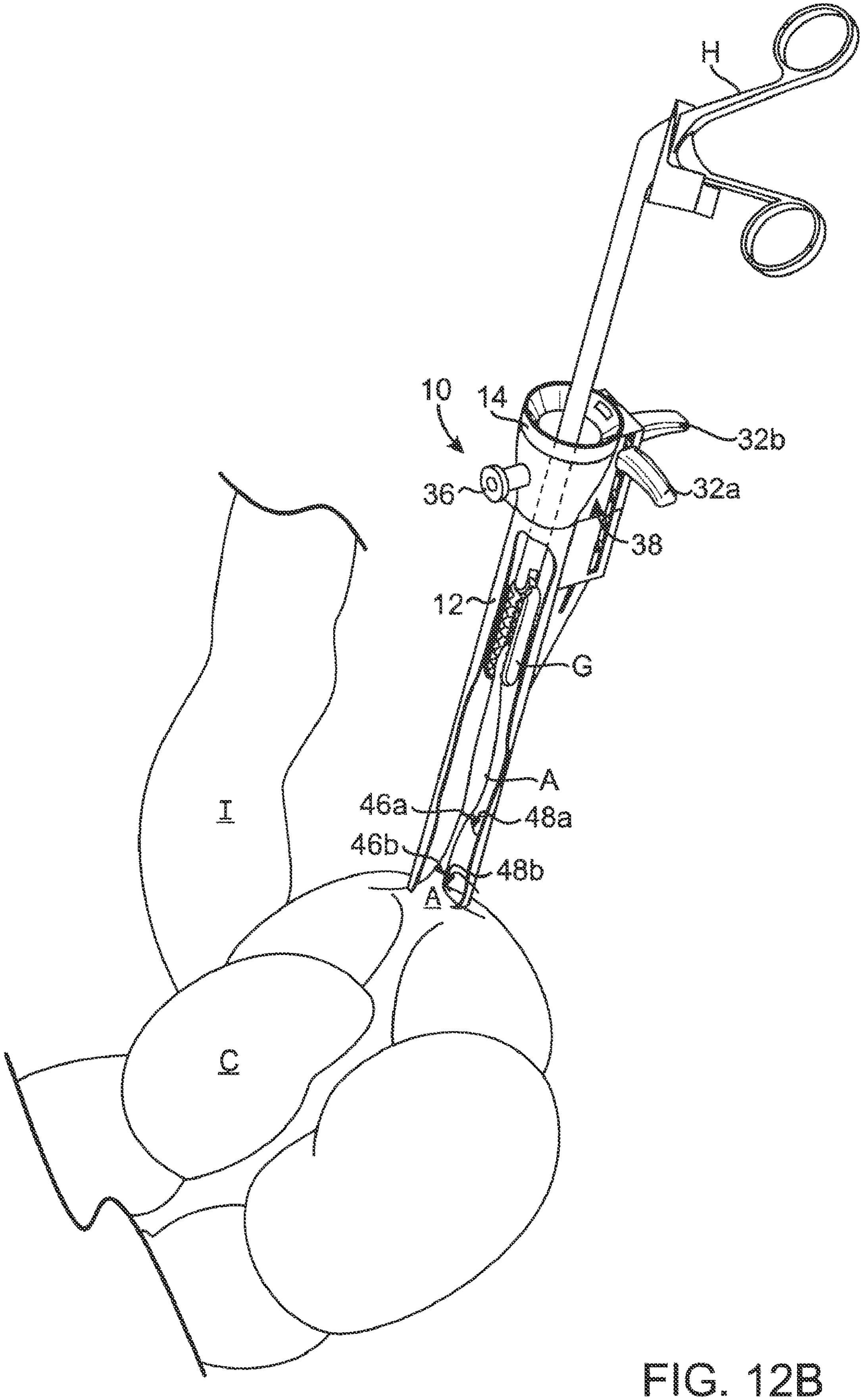
FIG. 12B is a perspective view of an embodiment of the trocar of FIG. 1, partially broken away, illustrating a ligated appendix in the grasp of the trocar assembly, and showing a useful embodiment of a handle of a grasping tool in the trocar assembly.

FIG. 12B is a schematic perspective view of the trocar of FIG. 1, partially broken away and illustrating the jaw or grasping end G gripping an appendix A at the distal end of the instrument and the operative handle portion H at the proximal end of the grasping tool. FIG. 1 shows within trocar 10 a proximal loop 46a formed of a length of ligature 42a around appendix A. When the surgeon pulls upwardly on arm 32a the attached ligature 42a is pulled proximally within covered slot 28 and proximal ligature filament loop 46a is likewise pulled, through slip knot 48a, inside of the trocar, tightening proximal loop 46a around the appendix. The ligature filament of which proximal loop 46a is formed is preferably not cut, broken or otherwise separated from the loop, so as to securely retain appendix A within body 12 of trocar 10 when the appendix is ultimately divided. One useful alternative for maintaining the divided appendix within body 12 of trocar 10 is to incorporate a locking device at proximal end 16 of trocar 10 to temporarily maintain the closed grasper holding the divided appendix A within barrel 12 of the trocar while the surgeon actuates first arm 32a to close proximal loop 46a. Such a locking device could be formed, for example, of a zip-tie or other suitable mechanism and still function within the scope of the invention. If the surgeon prefers to have the grasping tool removed from the trocar, other suitable means of maintaining the divided tissue inside of the trocar barrel, instead of, or in addition to the unsevered ligature filament 42a can be conceived that would also be acceptably useful.

Figure 12C:
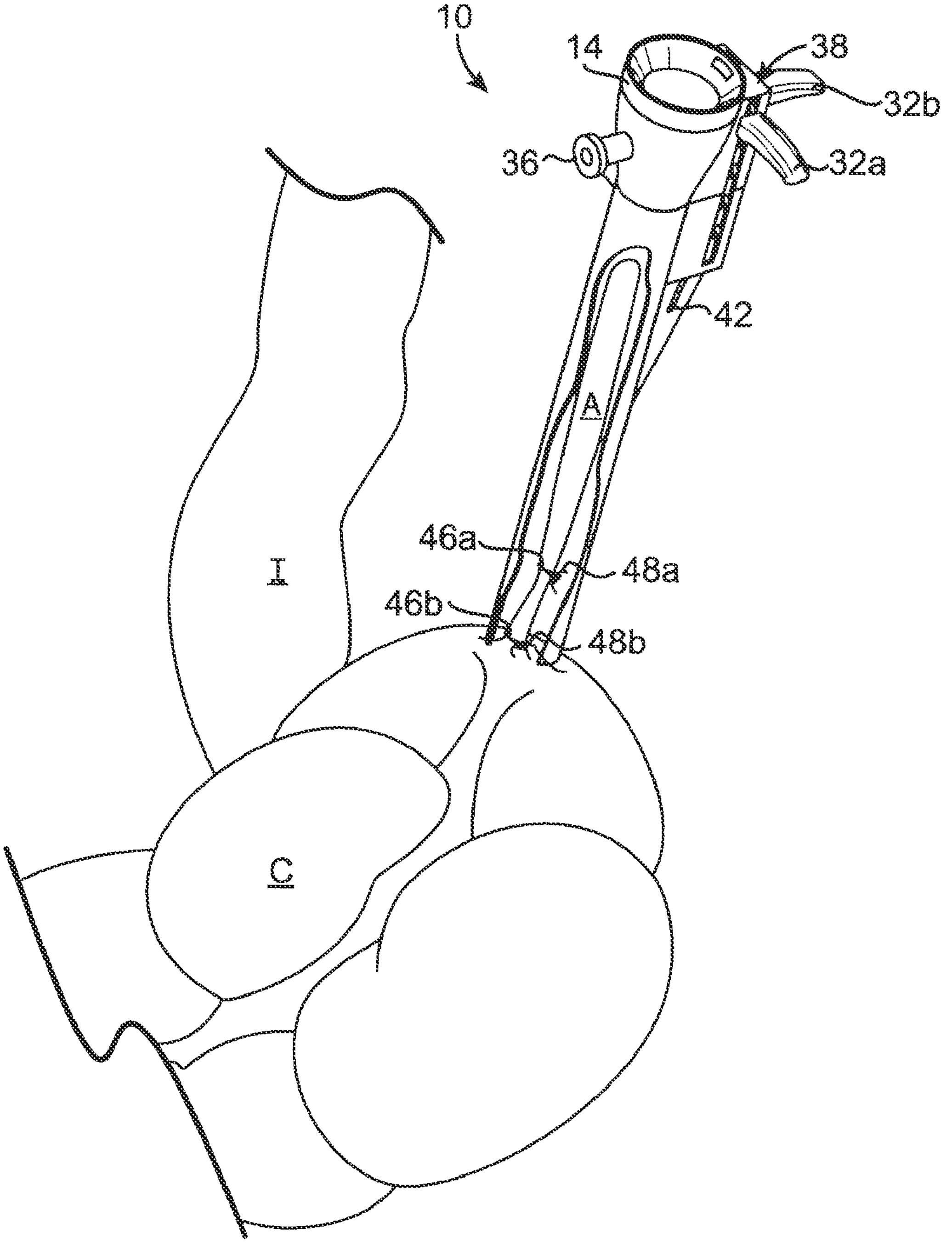
FIG. 12C is a perspective view of an embodiment of the trocar of FIG. 1 partially broken away, illustrating two ligatures on an appendix.

FIG. 12C illustrates the next step in the example laparoscopy procedure as performed with the present invention. Notably, the grasping device has been removed and appendix A is retained within body 12 of trocar 10 for ultimate disposal. Specifically illustrated is the secured distal filament loop 46b, below the already positioned proximal filament loop 46a. In the drawing loop 46b has been secured to the appendix a preselected distance closer to the cecum, in similar manner as previously described. The surgeon pulls arm 32b proximally along the corresponding arm track 34b (seen in FIG. 1) until loop 46b has reached a sufficient degree of tightness to tie-off that selected position on appendix A. When the surgeon is satisfied as to the position and secureness of distal ligature loop 46b, sufficient further proximal pressure is applied to corresponding arm 32b to cause filament ligature 42b to break beyond knot 48b. This breakage of ligature filament 42b can be successfully accomplished due, in part, to use of an appropriate surgical ligature material specifically designed to separate under sufficient pressure, acting as a mechanical fuse and leaving a short ligature "tail" of usually less than a few centimeters. Thus, no use of scissors or other cutting tool via an additional trocar is required in this preferred procedure. Alternatively, another useful embodiment can include a blade within the wall of trocar 10 to cut the distal ligature loop, replacing the function of the mechanical fuse in the ligature loop extension.

Figure 12D:
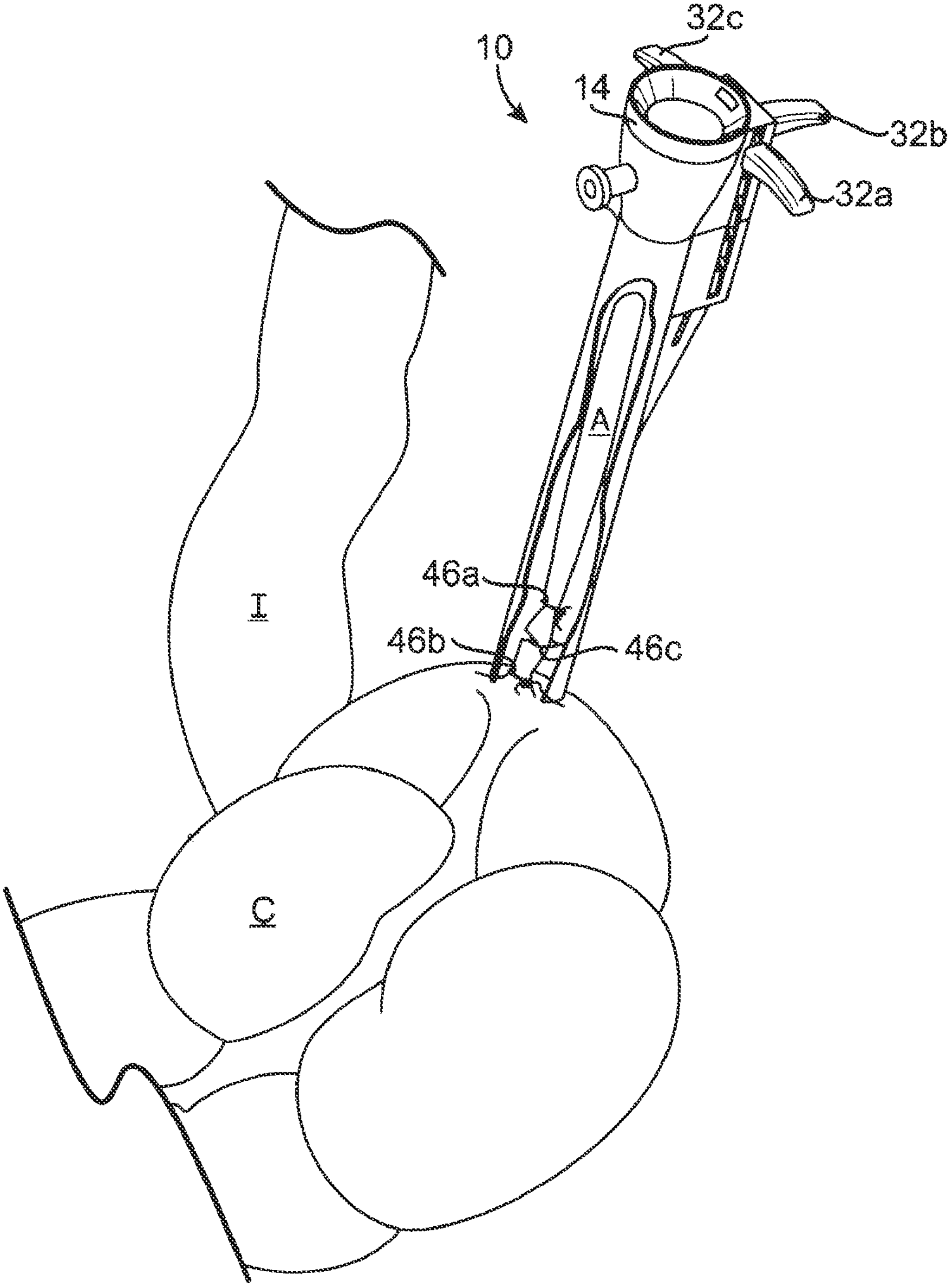
FIG. 12D is a perspective view of an embodiment of the trocar of FIG. 1, partially broken away, illustrating cutting of an appendix with a wire between two ligatures.

FIG. 12D illustrates the fourth step in the laparoscopic appendectomy example of use of the present invention. Reference to FIG. 3 is also suggested in order to see arm 32c and related elements which may be hidden from view in FIG. 12D. In this step the surgeon can pull up, proximally, on arm 32c, causing pulling of wire filament 46c at a preselected position on appendix A between ligature filament loops 46a and 46b. In this case, as in the preferred embodiment described above, wire 42c is preformed to include a distal loop 46c which is held in position by a weld 48c and thus no knot is required. Rather than tightening the loop, in this example, the pulling of wire 42c cuts through the appendix. It is particularly preferred, although not absolutely required, that wire 42c be first heated via connection of a known electrocautery device (not shown) at connection site 33, on hub 38, shown in this instance above (proximal to) arm 32c, to facilitate cutting and provide cauterization of the cut edges of the appendix. Just as in each of the above steps the surgeon's selected position for each arm or other suitable actuator is maintained in a corresponding track 34a, 34b, 34c by the spaced steps 40a, 40b, 40c which prevent back-sliding of corresponding arms 32a, 32b, 32c in each of their corresponding tracks. Other acceptable structures for maintaining any of the arms' positions can also be conceived, such as, for example, notches in the arm groove/track, or a ratcheting head that moves along a strap in one direction only, proximally in this case, in the manner of a so-called zip-tie, not shown.

Figure 12E:
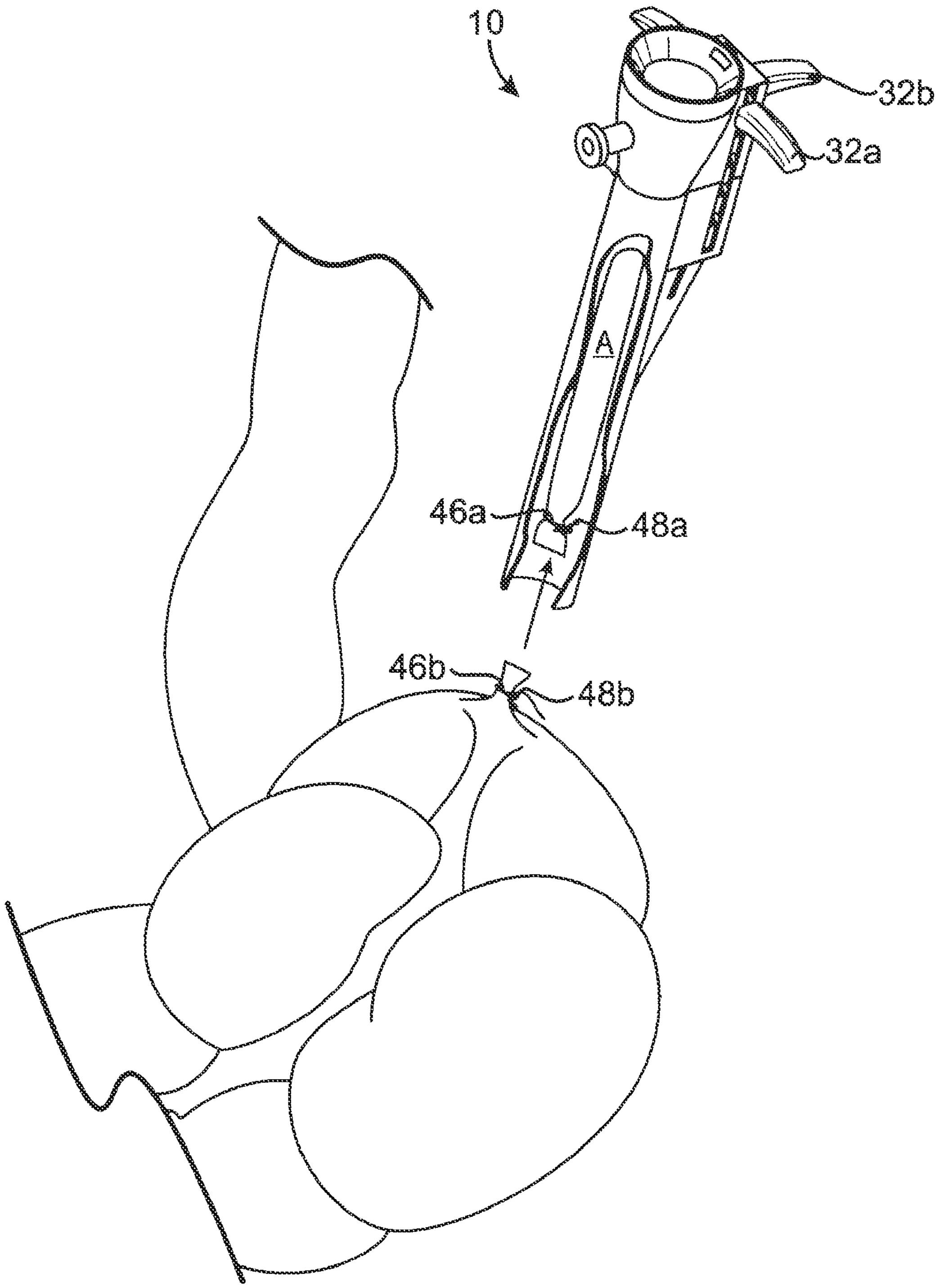
FIG. 12E is a perspective view of an embodiment of the trocar of FIG. 1, partially broken away, illustrating withdrawal of a divided appendix within the body of the trocar.

FIG. 12E illustrates the fifth step in the example procedure, wherein the divided appendix A is seen within the body 12 of trocar 10 as the trocar is being removed from the surgical site. The appendiceal stump on cecum C remains at the surgical site with the loop portion 46b and knot 48b of the distal ligature. Throughout the entire procedure the handling of the appendix has been accomplished in-line with trocar 10. The surgical site, of course is then closed, usually in a conventional manner. Throughout the laparoscopic appendectomy procedure an endoscopic light (not shown) can be of use in the normal fashion. This light can be one of a number of known varieties, or any light source newly developed which is appropriate for the surgical procedure.

To further elaborate on the features of the present invention, various suitable alternative embodiments include trocar 10 that is approximately cylindrical with an outside diameter of 22 mm, an inside diameter of approximately 18 mm, and an overall length of approximately 150 mm. Near the distal end of the trocar there are two ligatures 42a, 42b each having a sliding knot 48a, 48b, respectively, thereby each forming a ligature loop 46a, 46b. The ligature loops are preferably located in the distal end of trocar 10 and separated by about one cm, although other locations and separation distances can be conceived which may operate effectively. The filament loops 46a, 46b and 46c are formed so that each loop is predominately oriented in a plane and attached with a light film coating, adhesive, or other suitable material, to the internal wall of trocar 10 for temporary positioning. The planar normal preferably aligns approximately with the cylindrical axis of trocar 10. In this manner the loops are out of the way during introduction of the grasper and pulling in of the appendix, but the loops can still be deployed when needed, each at its own time for its own function.

Figure 11:
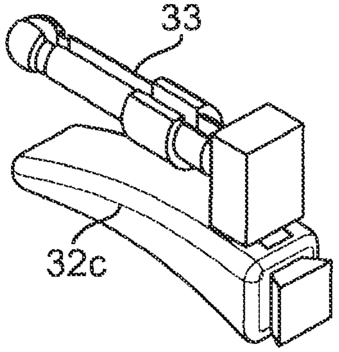
FIG. 11 is a perspective view of the electrocautery control arm of the trocar of FIG. 1.

Between the two ligature filament loops 46*a*, 46*b* is an electrocautery loop 46*c* which is also selectively removably attached to the internal wall of the trocar 10 and this loop is also approximately planar with its planar normal aligned with the cylindrical axis of the trocar 10. Each ligature loop 46*a*, 46*b* continues from its corresponding knot 48*a*, 48*b* as a ligature filament 42*a*, 42*b* through a corresponding aperture 44*a*, 44*b*, and then extends up the covered filament slot 28 (proximally), to a corresponding ligature proximal end that connects to a corresponding arm 32*a*, 32*b*. Similarly cutting filament wire 42*c* extends from its secured loop at the distal end of the wire through a hole in the trocar wall and up the slot 28 or path in the trocar cylinder 12 exterior. The hole size is small enough to prevent the corresponding knot from exiting the trocar and acts to cinch the ligature loop on the interior of the trocar body/cylinder. Similarly, to the ligatures 421, 42*b*, the electrocautery cutting wire 42*c* continues from its interior trocar loop 46*c*, through a hole 44*c* in the trocar wall, and up the ligature and wire filament slot 28 to a proximal filament end that connects to lever/arm 32*c* which is external to the trocar cylinder and is connected to the power source via connection 33. The lever-like arms are mounted externally via hub 38 in a secure manner, such as, for example, by interlocking to the external surface of trocar cylinder 12. The surgeon actuates the third arm 32*c* while it is powered by a power source, not shown, and connected via connection 33 (shown enlarged in FIG. 11) with a cutting current used to cut across tissue. A known electrocautery device, such as that known by the US registered trademark, Bovie®, Reg. U.S. Pat. No. 3,662,684, is one example of such a device.

In addition to the power source (not shown) and the arms on hub 38, the proximal end of the trocar has a gas portal 36 for selective introduction of carbon dioxide gas in known manner, to enhance visibility, as well as a known seal and valves to allow pressurization of CO2 within the body cavity of the surgical site. In the embodiment shown gas inlet 36 is positioned substantially opposite the center of a proximally directed end of hub 38. Inlet/portal 36 can also be reasonably placed in other useful positions on trocar 10 as well.

A suitable alternative embodiment of the present invention includes a suction tube which can be internal or external to the trocar. This added feature can be a suction passageway inside the wall of trocar body 12, an internal and/or an external suction tube attachment to the trocar, and/or all three options. In any of the conceived versions, providing suction to trocar 10 is useful to remove fluid and/or tissue to control bleeding, remove waste or tissue, or assist in visualization of the surgical site.

Acceptable alternative embodiments of trocar 10 include variations in the cross-section of the trocar, which may be elliptical or oblong, or any tubular cross section. In some embodiments it may be useful to have a different outside diameter, for example, of 25 mm or 28 mm, or any outside diameter for a trocar appropriate for the surgical procedure, which, as a reminder, may be some procedure other than the frequently performed appendectomy. An alternative inside diameter may also be a useful alternative, for example, an inside trocar diameter of 15 mm or 20 mm, or any inside diameter for a trocar appropriate for a surgical procedure and large enough to contain the intended tissue upon extraction. Similarly, a trocar with an alternative length will also be useful for some procedures. Thus, the new trocar with an overall length of 100 mm or 125 mm, or 175 mm or 200 mm or some other useful length could be preferred for a specific surgical procedure, even for an appendectomy for a certain patient. The aforementioned dimensions represent dimensions according to some embodiments but it will be appreciated that other dimensions may be used in various embodiments. Indeed, various embodiments contemplate any suitable dimension or set of dimensions consistent with any use of function of the device. References to length and/or diameter and/or cross-section shapes and/or to any other specifications are not to be seen as limiting as to the scope or/or the overall function of the device.

As the most distal ligature loop 44*b* is closed, the ligature within covered filament slot 28 acts as a mechanical fuse. The mechanical fuse functions because a portion of the ligature is weaker than the other portions of the ligature and thus breaks when an appropriate tension is applied. The appropriate tension is sufficient to ligate the tissue that is to remain in the body, yet will still allow the filament to break. The ligature mechanical fuse is necessary so that distal ligature loop 46*b* with knot 48*b* and an extending appropriate length of ligature tail 50 (usually about 1 cm) remains attached to cecum C when appendix A is removed with trocar 10. The length of tail 50 must be sufficient to prevent the knot from untying which might allow the ligated tissue adjacent the cecum to leak.

An alternative embodiment of the filaments is that the continuation is on the outside of trocar 10, or on the inside of the trocar, rather than traveling through covered slot 28. Another conceivable and useful alternative structure includes having two coaxial tubes as the trocar body where the ligature continues between the coaxial tubes, instead of in filament slot 28; having closure of a ligature loop by action of twisting the coaxial tubes of the trocar to actuate the loops; and closing of the ligature loops and electrocautery loops by action of relative axial translation of the coaxial tubes; i.e., telescopic tubing. A further acceptable alternative for closing of the filament loops entails axial sliding or coaxial twisting of coaxial trocar tubes to control the order of closure of the filament loops via the relative amount of slack of the ligatures and electrocautery wire.

Regarding the electrocautery wire 42*c*, trocar 10 can alternatively include a cutting wire that is abrasive, or a wire of small enough diameter to act as a sharp cutting tool. A still further alternative is to use a surgical knife or scalpel in place of the electrocautery wire, or to use a cutting shutter, structured and triggered somewhat like the shutter of a camera. In each case the cutting mechanism will be within trocar body 12 and actuated by an additional arm or other suitable actuator.

Further conceivable and acceptably useful alternative structures and procedures for purposes of closing the filament (ligature or wire) loops 46 include e.g., by winding the filament around a shaft with a crank or a motor; by pulling on the filament by hand or with an external tool; or by use of magnetic forces to pull on a filament to close the associated loop.

Some alternative and useful embodiments include providing the filaments with a coating of a coagulation agent, or to disperse a coagulation agent into the surgical field by action of the filament arms, or by action of at least one additional alarm, button or other actuator on trocar 10.

Trocar 10 is preferably formed of a substantially transparent material in order to allow visualization of the tissue, ligatures and electrocautery cutting wire inside the trocar via a laparoscope or any other method that allows visualization inside the body cavity. Useful examples of this material include acetal copolymer and high-density polyethylene. Other useful materials may also presently exist or may be developed which are also suitable. Materials that are translucent or opaque may offer sufficient visualization to be acceptable, if not preferred. It is preferred that the primary materials of which the new trocar 10 is formed be relatively inexpensive and suitable for a single use prior to being disposed of appropriately.

While it is conceivable that trocar 10 could be formed of other materials, such as stainless steel or other substances that can be sterilized, refilled, and/or reused, and still be within the scope of the invention, from the perspective of convenience of use, economy and sterility, these materials would not be most preferred. Nonetheless, if a transparent material is not used to form the body of trocar 10, such an embodiment can alternatively include a camera attachment to the distal end of the trocar, or to the proximal end with known fiber optics located distally. In either case, the camera is used to visualize the division of the appendix or for other surgical visualization purposes.

It is to be understood that while the preferred embodiment describes trocar 10 as having a straight tubular body 12, as illustrated, other acceptable and useful alternatives may include the body of trocar 10 having a shape that is a curved tube, tapered one-way or two-way, or having a varying cross-sectional shape. The varying or changing cross-section can improve the ability of the trocar to capture, hold, or extract the appendix with the trocar. Further, the varying cross-section can improve the ability of the trocar to enter the body cavity, depending upon the particular laparoscopic surgical procedure to be performed.

Figure 13:
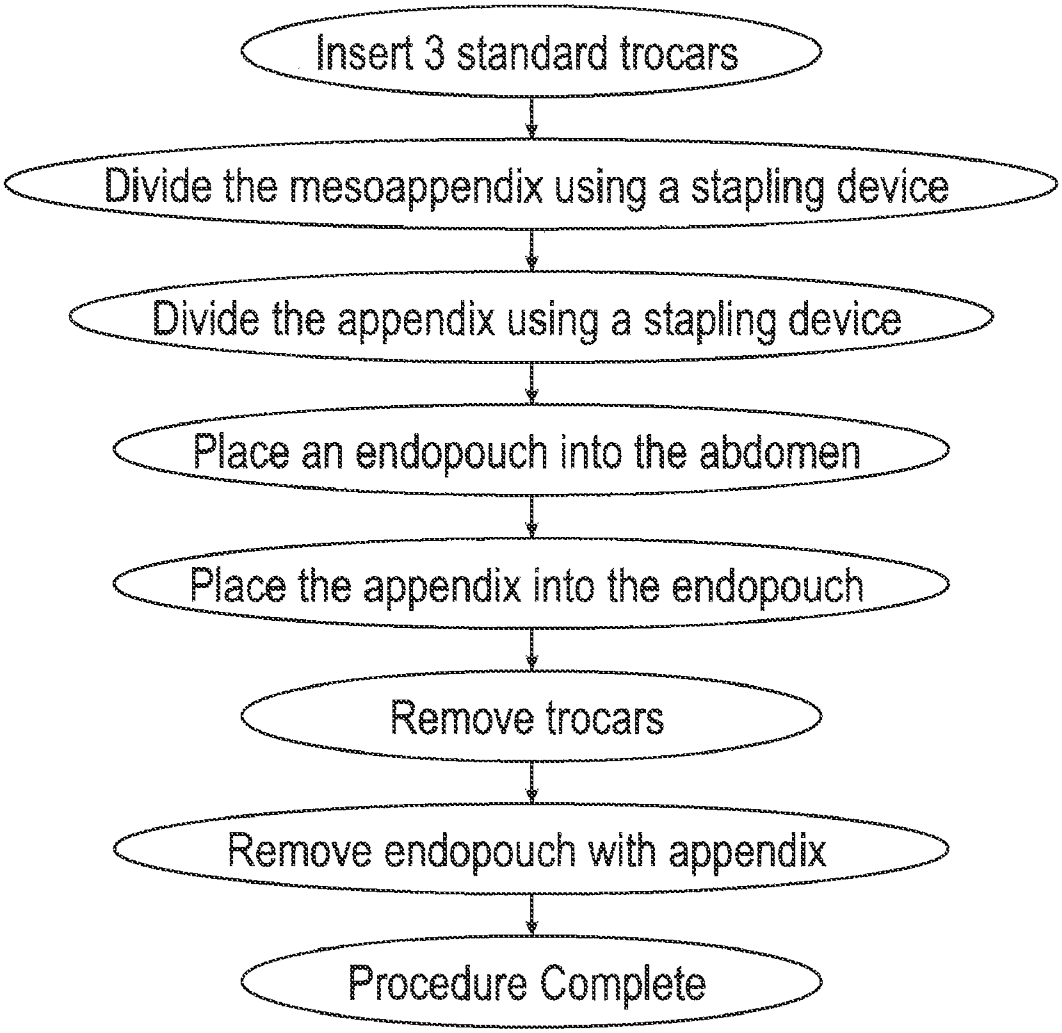
FIG. 13 (PRIOR ART)
FIG. 13 is a diagrammatic representation providing the steps of a conventional laparoscopic appendectomy operation utilizing known endo-stapling devices (prior art).
Figure 14:
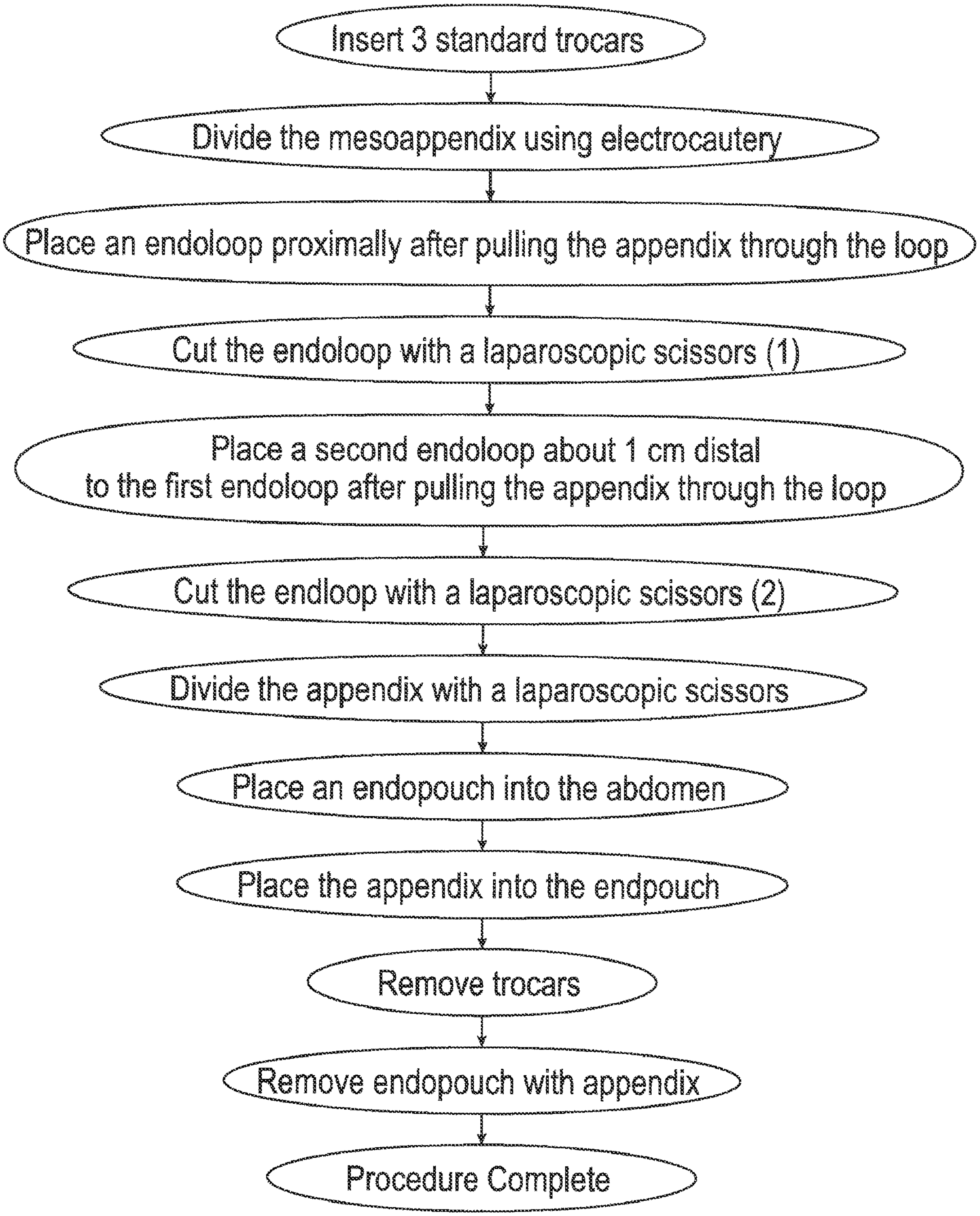
FIG. 14 (PRIOR ART)
FIG. 14 is a diagrammatic representation providing the steps of a conventional laparoscopic appendectomy operation utilizing known endo-loop ligatures (prior art).

FIGS. 13 and 14 (both prior art) are schematic layouts of the typical steps required in two well-known, typically performed laparoscopic appendectomy operations. They are presented for contrast with the procedure shown in FIG. 15, which is an example of a procedure performed with the presently described and claimed trocar 10. The procedure illustrated in FIG. 13 includes the use of a known endo-stapler as a surgical tool for dividing the mesoappendix and dividing the appendix. The illustrated procedure also requires use of a known endo-pouch to which the divided appendix is transferred for removal after removal of the various trocars.

The known procedure illustrated in FIG. 14 (prior art) requires multiple trocars (at least three), at least two endo-loops and at least one endo-pouch for removal of a divided appendix from the surgical wound, separately from the trocar. This procedure also requires dividing the mesoappendix, but in this instance using an electrocautery device instead of a stapling device. The two endo-loops are placed on the appendix and laparoscopic scissors are used to cut the endo-loops and to divide the appendix. It is important to understand that such known endo-loops are effectively additional surgical instruments having a handle with an attached floppy filament loop which must be manually placed at the desired location before manually tightening the loop around the chosen tissue. After cutting of the endo-loops the remainder of each of the endo-loop instruments is then removed from the surgical site.

Figure 15:
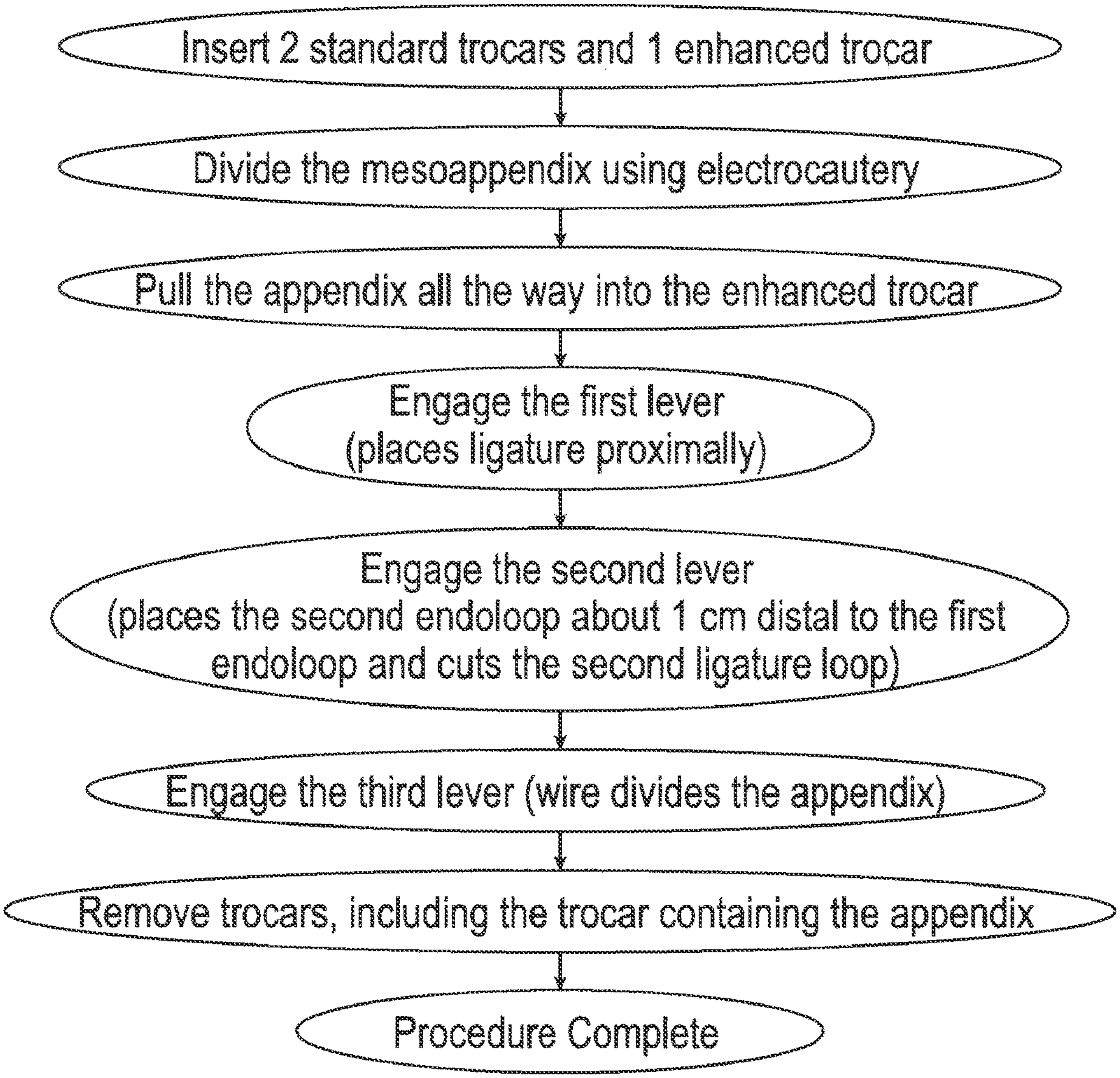
FIG. 15 is a diagrammatic representation providing the steps of a laparoscopic appendectomy operation, enabled by a trocar with two ligature loops and an electrocautery loop in keeping with the present invention.

FIG. 15 schematically illustrates one example of a laparoscopic appendectomy operation enabled by a useful embodiment of the presently disclosed trocar 10, with two ligature loops and an electrocautery/wire loop as elements of the new enhanced trocar itself. When following the steps outlined in FIG. 15 and keeping in mind the structure of the new trocar 10, with all the ligatures, cutting device and storage of the divided appendix being part of the new trocar as a unit, instead of as several separate instruments, it is clear that enhanced trocar 10 provides the surgeon with means by which to perform a well-known surgical procedure in a much more efficient manner, reducing the number of actual separate instruments handled, placed into the patient and then removed therefrom. The present in-line procedure requires less time and is less invasive, and is much simpler and faster to perform. The efficiency of the new procedure with the enhanced trocar also reduces surgeon fatigue, providing multiple benefits within the surgical system.

Figure 16:
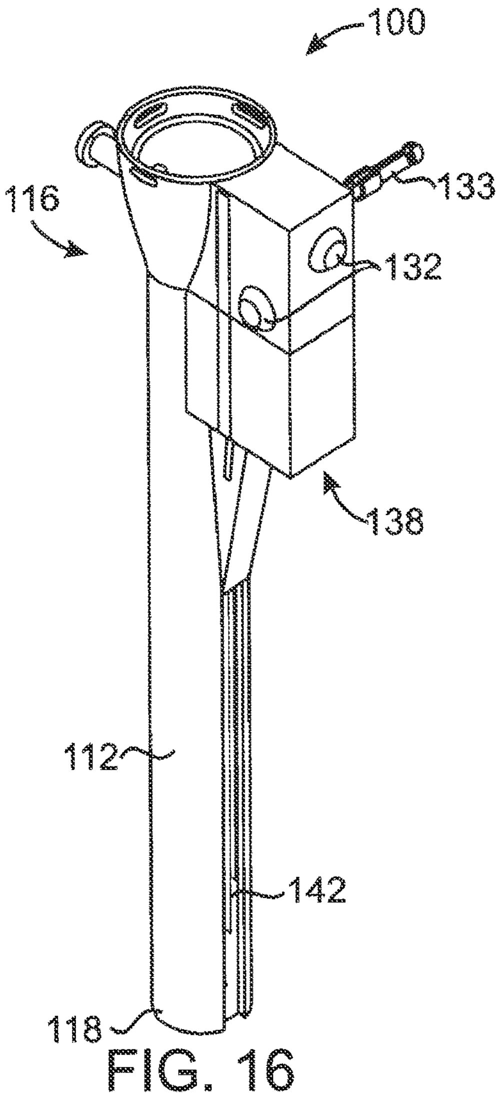
FIG. 16 is a perspective view of an alternative embodiment of an enhanced trocar constructed in accordance with and embodying the present invention, featuring a motorized mechanism of operation.

FIG. 16 illustrates one alternative practical embodiment of an enhanced trocar 100 of the present invention, in which the hub carrying the arms for controlling the filaments has been replaced with a motorized version. The hub 138 in this embodiment houses small motors (not seen) that connect to and wind up the filaments. In this example there are two buttons 132 (rather than arms) on the housing, one for control of both of the two ligation filaments and one for a cutting filament, e.g., the surgical wire. The electrocautery connection 133 can be the same as in the initial embodiment described and shown. Other aspects of this embodiment are the same or similar to those described in detail with reference to the first embodiment.

Figure 17:
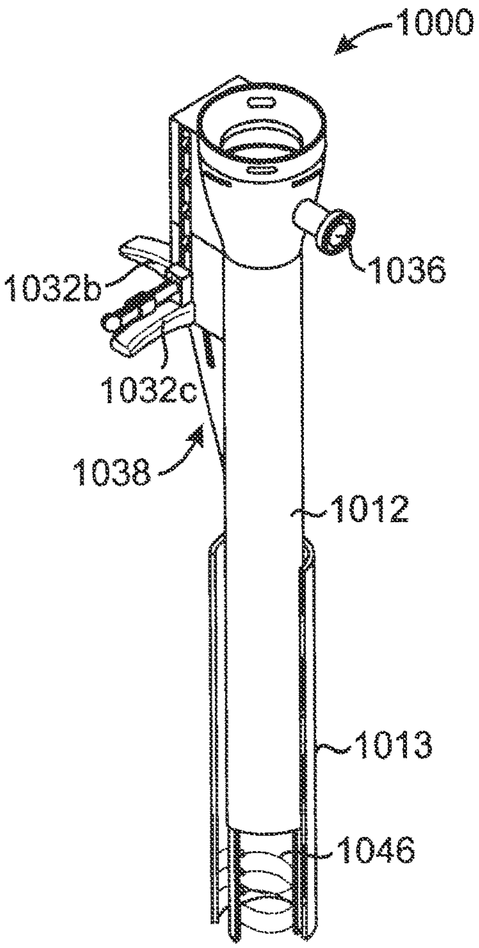
FIG. 17 is a perspective view of a further alternative embodiment of an enhanced trocar constructed in accordance with and embodying the present invention, featuring a double-walled twisting mechanism of operation.

It is conceived that a useful embodiment of the new enhanced trocar will include an inner cylinder to protect and retain the filament loops and while the trocar is inserted into the body of the patient and the tissue to be removed is pulled into the trocar tube, the inner cylinder would be twisted, causing closure of the ligature loops and electrocautery wire onto the tissue. For example, FIG. 17 illustrates an alternative embodiment 1000 of the present invention. In this example the trocar body 1012 is formed of two concentric and rotatable tubes, with the necessary filaments passing between the walls of the two tubes. The filaments are attached to the inner surface of the outer tube such that rotation of the tubes relative to each other creates tension on the filaments. For example, an outer wall (tube) could be provided exterior of the body 12 of the original enhanced trocar, or some similar construction. In this manner a walled trocar can be visualized and the operation thereof understood. In this embodiment the two walls can be twisted or rotated relative to each other, until the filament forming the lowest (distal) surgical ligature loop breaks away, as described above, as a mechanical fuse. The drawing shows one arm for connection to and operation of a cutting filament/wire or other cutting device, and an electrocautery connection mounted on a hub 1038 at the proximal end of the trocar 1000. Other aspects of this embodiment are the same or similar to those described in detail with reference to the first embodiment.

As used herein, “embodiment” refers to “embodiments” (i.e., in the plural), and does not imply that there is only a single manner of making or using the subject matter described therein, unless otherwise specified. The two alternative embodiments shown and described are intended only as representative reasonable and useful alternatives to the primary structure of this document.

As used herein, “alternative embodiment(s)” may refer to a second embodiment or second embodiments that are discussed in relation to a first embodiment or first embodiments. One or more aspects of the second embodiment or embodiments (e.g., one or more components; e.g., one or more process steps) may differ with respect to analogous aspects of the first embodiment or embodiments. For example, in the second embodiments, a component used in the first embodiments may be absent, built differently, attached differently, shaped differently, used differently, sized differently, marked differently, cleaned differently, or may otherwise differ from its analog in the first embodiments. As another example, the second embodiments may utilize components, may have different overall construction than do the first embodiments, may have different overall size and/or shape in relation to the first embodiments, or differ in any other way from the first embodiments. However, it will be appreciated that first embodiments and second embodiments may share one or more common aspects or features, or indeed that first embodiments and second embodiments may share most (or nearly all) aspects or features in common. It will also be appreciated that first embodiments and second embodiments are not necessarily mutually exclusive unless otherwise specified.

It will be appreciated that the use of the words "alternative embodiment(s)," "alternate embodiment(s)," or the like, does not state or imply any preference for a first embodiment, a second embodiment, or any other embodiment, unless otherwise specified.

The foregoing description of specific embodiments of the present invention is for purposes of illustration and description. They are not intended to be exhaustive or to limit the invention to the precise forms disclosed and many modifications and variations are possible in light of the above teaching. For example, different types of materials may be known or may be later developed that will be suitable for substitution with those presently described. The embodiments were chosen and described in order to explain the principles of the invention and its practical applications, to thereby enable others skilled in the art to best utilize the invention and various embodiments with various modifications as are suited to the particular use contemplated.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An enhanced trocar for laparoscopic surgery, the trocar comprising a proximal end, a distal end and a tubular trocar body connecting and extending between the proximal end and the distal end, the trocar body being shaped and sized to receive inline and retain therein tissue isolated and divided during a laparoscopic surgical procedure, thereby permitting a surgeon to remove such tissue from a surgical site and dispose of the removed tissue without an additional dedicated disposal device, the trocar having at least one mechanism for isolating and/or dividing the tissue within the body of the trocar;

wherein the at least one mechanism for isolating and/or dividing tissue within the body of the trocar comprises at least one surgical filament connected to the trocar;

wherein one of the at least one surgical filament connected to the trocar comprises a first surgical filament connected to the proximal end of the trocar and extending toward the distal end of the trocar;

wherein the at least one surgical filament for isolating and/or dividing tissue within the body of the trocar includes a first surgical ligature and a second surgical ligature;

wherein at least one of the first surgical ligature is formed to selectively break-away, to thereby permit release from the trocar of any tied-off tissue remaining at the surgical site;

wherein the first surgical ligature and the second surgical ligature are each operably connected to the hub for selective manipulation by the surgeon;

wherein the first surgical ligature and the second surgical ligature are each provided with a ligature loop and a sliding ligature knot at respective distal ends of the first surgical ligature and the second surgical ligature, to thereby permit selective manipulation by the surgeon of the first surgical ligature and the second surgical ligature to separately set the tension of the respective ligature knots and cause tightening of the respective loops thereof to selectively tie-off tissue during a surgical procedure while the tissue is within the body of the enhanced trocar;

wherein the at least one surgical filament connected to the trocar for isolating and/or dividing tissue within the body of the trocar comprises a surgical wire operably connected to the proximal end of the trocar and extending toward the distal end of the trocar body;

wherein the surgical wire has a loop at the distal end thereof, the loop being removably attached around an interior wall of the trocar body to thereby permit selective release and manipulation by the surgeon of the wire loop to divide tissue within the trocar body;

wherein the first ligature loop and the second ligature loop are each removably attached around an interior wall of the trocar body, so as to avoid interfering with the path of any surgical instruments passing through the distal end of the trocar until either or both of the first ligature loop and the second ligature loop is selectively released from the interior wall of the trocar by the surgeon;

wherein for each of the first surgical ligature and the second surgical ligature, the trocar has a corresponding aperture in the trocar body wall for passage therethrough of the corresponding surgical ligature, and further wherein the loop at the distal end of each surgical ligature is connected to the corresponding surgical ligature loop inside of the corresponding aperture by a slidable knot, wherein proximal urging of a ligature by the surgeon causes closing of the corresponding surgical ligature loop through the knot and around any tissue therein;

further comprising at least one surgical filament control device connected to the proximal end of the trocar for selective operation thereof by the surgeon for precise placement of the at least one surgical filament;

wherein the at least one surgical filament control device includes at least one arm operably connecting the at least one surgical filament to the proximal end of the trocar to thereby permit the surgeon to selectively move the at least one surgical filament within the trocar;

wherein the at least one surgical filament control device includes a hub connected at the proximal end of the trocar, the hub having at least one track extending on the trocar, each track of the at least one track being for receipt and adjustable carriage of a corresponding arm, each arm being connected to a proximal end of a corresponding surgical filament.

2. The enhanced trocar of claim 1, wherein the at least one track has a series of spaced-apart physical stops to facilitate accurate and secure placement in the at least one track of a corresponding arm at a selected site therein.

3. The enhanced trocar of claim 2, wherein the at least one arm comprises a first arm, a second arm and a third arm, the first arm being attached to a proximal end of a first surgical ligature; the second arm being attached to a proximal end of a second surgical ligature and the third arm being attached to a proximal end of a surgical wire.

4. The enhanced trocar of claim 1, further comprising a slot formed in an exterior surface of the tubular wall of the trocar body, for passage of the at least one surgical filament within the slot.

5. The enhanced trocar of claim 4, further comprising a cover for enclosing the slot.

6. The enhanced trocar of claim 1, further comprising at least one motor attached to the trocar body for powering selective operation by the surgeon of at least a portion of the at least one mechanism for isolating and dividing the tissue within the body of the trocar.

7. The enhanced trocar of claim 1, wherein the at least one mechanism for isolating and dividing the tissue within the body of the trocar includes a concentric double wall for passage therebetween of the at least one surgical filament.

8. A method of performing a laparoscopic surgical procedure comprising the steps of:

a) providing the enhanced trocar of claim 1 to a surgeon;

b) inserting two standard trocars and the enhanced trocar into the abdominal cavity of a surgical patient;

c) dividing tissue to be removed from the abdominal cavity;

d) grasping the tissue to be removed and pulling it entirely into the enhanced trocar body;

e) engaging the first arm to thereby secure the first ligature loop within the enhanced trocar and proximally around the tissue to be removed;

f) engaging the second arm to thereby secure the second ligature loop within the enhanced trocar body distally and spaced-apart from the first ligature, and applying sufficient pressure to cause the second ligature to break away from the second ligature loop;

g) engaging the third arm, to thereby cut through the tissue with the surgical wire within the enhanced trocar body between the first ligature loop and the second ligature loop;

h) removing all trocars from the surgical site, the enhanced trocar body containing the tissue removed; and i) closing the wound to complete the laparoscopic surgical procedure.

* * * * *